United States Patent [19]

Sanchez et al.

[11] Patent Number: 5,494,936
[45] Date of Patent: Feb. 27, 1996

[54] DELIVERY FORMULATION FOR PROBUCOL

[75] Inventors: Robert A. Sanchez, Carlsbad; Sheldon S. Hendler, La Jolla, both of Calif.

[73] Assignee: Vyrex Corporation, La Jolla, Calif.

[21] Appl. No.: 263,908

[22] Filed: Jun. 22, 1994

Related U.S. Application Data

[63] Continuation of Ser. No. 53,898, Apr. 27, 1993, abandoned, which is a continuation-in-part of Ser. No. 874,774, Apr. 27, 1992, abandoned.

[51] Int. Cl.⁶ .................................................. A61K 31/10
[52] U.S. Cl. ............................................................ 514/712
[58] Field of Search .............................................. 514/712

[56] References Cited

U.S. PATENT DOCUMENTS 4,985,465  1/1991  Hendler .................................. 514/712

OTHER PUBLICATIONS

Hegg et al., J. of Pharm. Sci., 73(12), pp. 1758–1763 (1984).
Palin et al., J. Pharmacy & Pharacology, 35, p. 85p (1983).

*Primary Examiner*—Kimberly Jordan
*Attorney, Agent, or Firm*—Townsend and Townsend and Crew

[57] ABSTRACT

A lipophilic pharmaceutical formulation including a digestible vegetable oil and a phenolic antioxidant such as probucol is disclosed for oral administration. The probucol will typically be present in an amount of between 5 and about 15% by weight and the digestible vegetable oil will be present in an amount of between about 80 and 95% by weight. A small quantity of ethanol may be added to the formulation to increase the solubility of probucol. The formulations will be orally administered for treatment of hypercholesterolemic patients and others suffering from certain ailments.

18 Claims, 5 Drawing Sheets

DELIVERY FORMULATION FOR PROBUCOL

CROSS-REFERENCE TO RELATED APPLICATIONS

This is a Continuation of application Ser. No. 08/053,898, filed Apr. 27, 1993, now abandoned, which is a Continuation-In-Part of U.S. Ser. No. 07/874,774, filed Apr. 27, 1992 (Sanchez and Hendler inventors), now abandoned, which is incorporated herein by reference for all purposes.

BACKGROUND OF THE INVENTION

The present invention lies in the field of lipophilic pharmaceutical formulations for oral administration. More specifically, the present invention lies in the field of pharmaceutical formulations including a digestible vegetable oil and a phenolic antioxidant such as probucol.

Probucol is a commercially available drug marketed under the trademark Lorelco® (Marion Merrell Dow Pharmaceuticals, Inc., Kansas City, Mo.). It is a water-insoluble antioxidant, chemically related to the widely used food additives 2,[3]-tert-butyl-4-hydroxyanisole (BHA) and 2,6-di-tert-butyl-4-methylphenol (BHT). Today, probucol is used primarily to lower serum cholesterol levels in hypercholesterolemic patients. However, recent work has shown that it may also be used to treat viral infections such as AIDS. The anti-viral properties of probucol are discussed in U.S. Pat. No. 4,985,465, which is assigned to Vyrex Corporation (the assignee of the present invention) and incorporated herein by reference for all purposes.

Probucol's chemical name is bis(3,5-di-tert-butyl-4-hydroxyphenyl) acetone mercaptole, and it has the following structure:

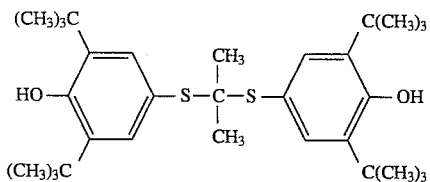

Probucol is commonly administered in the form of tablets containing celluloses and other excipients. This form of probucol is poorly absorbed into the blood, and is excreted in a substantially unchanged form. Further, the tablet form of probucol is absorbed at significantly different rates and in different amounts by different patients. In one study (Heeg et al., *Plasma levels of probucol in man after single and repeated oral doses.* La Nouvelle Presse Medicale, 9(40), 2990–2994 (1980)), peak levels of probucol in sera were found to differ by as much as a factor of about 20 from patient to patient. These results are presented in FIG. 1 which shows how the concentration of probucol in blood changed with time in six patients who received a 250 mg dose. (FIG. 1 is a reconstruction of a semilogarithmic plot presented in the above article).

Because the tablet form of probucol has these various problems, an alternative delivery means having improved absorption characteristics would be highly desirable. An oil-based delivery vehicle might be expected to improve absorption of oral doses, as probucol is substantially water insoluble. However, very little work has been performed in this area. Two publications do describe studies in which probucol was administered to rats via oil-containing formulations, but neither of these publications describes a formulation optimized for high absorption and uniform absorption. In addition, neither of these studies involved a direct comparison of tablet-form and oil-containing delivery vehicles. Thus, it is possible that the formulations described in these references performed no better than the Lorelco® tablets.

One of these references (J. F. Heeg et al., *Pharmacokinetics of probucol in male rats.* Journal of Pharmaceutical Sciences, 73 (12), 1758–1763 (1984)), describes the use of an emulsion of water and coconut oil to orally deliver probucol to a series of test rats as part of a pharmacokinetic study. The emulsion was prepared by combining a solution of approximately 1% probucol in coconut oil (a naturally occurring saturated medium chain triglyceride) with an aqueous mixture of glucose, lecithin and detergent. This emulsion was administered to the rats orally through stainless-steel feeding needles. At certain times after administration, selected rats were decapitated and exsanguinated to test the plasma distribution and clearance of probucol. The absorption results were unimpressive, prompting the authors to conclude that the formulation gave poor availability, and that further studies of oil-based delivery vehicles were needed. Further, because only two rats were analyzed at each time point, this study could not show whether the probucol is uniformly absorbed from individual to individual.

In another study (K. J. Palin et al., *The effect of oil on the absorption of probucol in the rat.* Journal of Pharmacy and Pharmacology, 35 (supplement) 85P (1983)), investigators measured the plasma concentration of probucol in rats orally administered solutions of probucol in peanut oil and in medium chain triglyceride. The concentration of probucol used in the test solutions was not disclosed. Single oral dosages of the solutions were administered to groups of 4 rats in doses of 100 mg/kg body weight. Surprisingly low rates of absorption were observed, as shown in their results presented in Table 1.

TABLE 1

| $_{16}(\mu g \cdot hr/ml)$ | $C_p(max)$, μg/ml | $T_{max}$(hrs) | $AUC_0$ |
|---|---|---|---|
| probucol in medium chain triglyceride | 0.54 ± 0.1 | 7 ± 2 | 4.57 ± 1.0 |
| probucol in peanut oil | 1.73 ± 0.2 | 5 ± 2 | 11.74 ± 1.6 |

The above discussion shows that a need still exists for an optimized probucol delivery formulation. The desired formulation should be readily absorbed by the patient and should reach a high plasma concentration for a given dose. It should also exhibit absorption characteristics that do not vary greatly from individual to individual.

SUMMARY OF THE INVENTION

The present invention provides improved lipophilic pharmaceutical formulations for oral administration. In particular, the formulations of this invention contain greater than about 5% by weight of probucol in a digestible vegetable oil. It has been found that such formulations exhibit superior absorption into mammalian sera. Specifically, the formulations of the present invention are absorbed more rapidly, more uniformly, and more completely than is possible with tablet formulations. Thus, probucol is administered in a safe predictable manner and will be absorbed at fairly uniform concentrations from individual to individual.

In preferred embodiments of the present invention, probucol will be present in solutions at concentrations of greater than about 5% by weight, with the balance being primarily a digestible vegetable oil. It may be desirable to add a small quantity of ethanol or another pharmaceutically acceptable organic solvent to increase the solubility of probucol in the vegetable oil and/or prevent precipitation during storage or refrigeration. If ethanol is used, it is preferably present in a concentration of less than about 10% by weight and more preferably in a concentration of about 5% or less by weight. Regardless of whether ethanol is present, the probucol will preferably be present in amounts of between about 5 and 15% by weight, more preferably between about 8 and 13% by weight, and most preferably about 10% by weight. The digestible vegetable oil will preferably be either a medium or long chain triglyceride, preferably a medium chain triglyceride such as Neobee M5 (Stepan Co., Maywood, N.J.) or Miglyol 812 (Dynamet Nobel, Troisdorf, Germany). Other suitable vegetable oils include peanut. oil, corn oil, safflower oil, olive oil, soybean oil, etc.

The present invention is also directed to methods of orally administering probucol to an organism—such as a human—by way of formulation including at least about 5% by weight probucol in a digestible vegetable oil. In some cases the formulation will be administered to lower serum cholesterol and in other cases it will be administered to treat other ailments such as viral infections. Preferably, the formulation will be administered in daily doses of between about 5 and about 40 milligram probucol per kilogram of body weight. Alternatively, the formulation will be administered in doses of between about 100 and 1000 mg/day probucol, and more preferably between about 200 and 800 mg/day. Of course, the dosage may vary depending upon the severity of the patient's condition, the patient's strength, and the type of ailment, as is well known in the art.

A further understanding of the present invention may be obtained by the following discussion and associated examples.

DESCRIPTION OF SPECIFIC EMBODIMENTS

Figure 1:
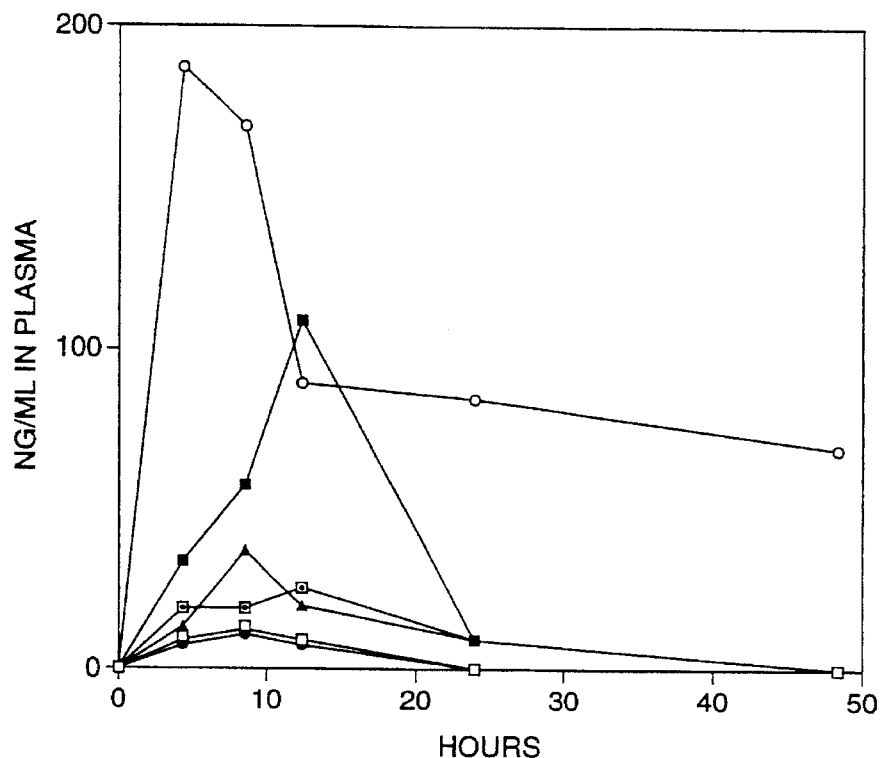
FIG. 1 is a graph of the concentration of probucol in blood versus time for six patients who received a 250 mg dose of Lorelco®.

The present invention provides an improved delivery vehicle for probucol., Specifically, it has been found that solutions of probucol at certain concentrations in triglyceride oils provide superior performance for the oral delivery of probucol.

Some preferred formulations of the present invention will include about 5 to about 15 weight percent probucol in a triglyceride. More preferably, the probucol will be present at about 8 to 13% by weight and most preferably at about 10% by weight. Preferably, the probucol will be completely dissolved in the triglyceride. Other materials may be added to the formulation in addition to the triglyceride and probucol, so long as these other materials do not substantially contribute to the activity or action of the probucol and the delivery vehicle. For instance, a small amount of ethanol may be added to the formulation to increase the solubility of probucol and prevent probucol from precipitating during long periods of standing or refrigeration. Other cosolvents such as acetone may also be used. Still other components may be added such as emulsifying agents like lecithin. However, the additional materials should not profoundly effect the physiological activity, stability, or physical form of the formulation. For instance, formulations having substantial amounts of insoluble components such as water or other polar solvents which tend to form emulsions are not preferred.

Digestible vegetable oils are a preferred form of triglyceride solvent for probucol in this invention. As used in this invention, a "vegetable oil" is any oil deriving from a vegetable source as well as certain synthetic equivalents of vegetable oils. Preferred vegetable oil solvents for probucol include medium chain triglycerides, coconut oil, and peanut oil. Medium chain triglycerides include vegetable oils with side-chains containing from 6 to 12, and preferably from 8 to 10 carbon atoms. One or more of the side chains may be saturated, monounsaturated, or polyunsaturated. Preferred synthetic equivalents of naturally occurring vegetable oils will be digestible and may not, however, be found naturally in plants. Examples of synthetic equivalents of naturally occurring vegetable oils include, for example pure, uniform chain length preparations of triglycerides such as trilaurin (C12), trimyristin (C14), tripalmitin (C16), tristearin (C18) and many others. One manufacturer of such synthetic triglycerides is Nu Chek Prep, Inc., Elysian, Minn.

In many instances, the formulations of the present invention may be made by simply combining the various components (e.g. probucol and peanut oil) and stirring at room temperature until the probucol completely dissolves. In some instances, however, it may be desirable to dissolve the probucol at elevated temperatures to more rapidly achieve a complete solution. When a cosolvent such as ethanol is used, solubilization is achieved more rapidly.

The probucol formulations of the present invention can be administered to humans in daily dosage ranges of preferably about 5 to about 40 milligrams per kilogram of body weight, more preferably about 10 to about 30 mg/Kg. In the most preferred embodiments, the daily dosage will be about 15 mg/Kg. However, this dosage may vary depending upon the severity of the patient's condition and the type of condition being treated. Those of skill in the art will readily be able to determine what dose ranges are appropriate. Different preferred ranges may be appropriate for treatment of other ailments, as opposed to treatment of high serum cholesterol.

Depending upon the concentration of probucol in vegetable oil, the total amount of formulation administered to a patient will vary. If a large dose of probucol is required for the condition being treated, it may be desirable to administer a formulation containing a high concentration of probucol, e.g. greater than about 10% by weight. Of course, if the patient can tolerate it, a large dose may be provided by administering a large quantity of a low probucol concentration formulation.

EXAMPLE I

Three specific formulations of the present invention were prepared and tested against Lorelco® in pharmacokinetic studies described below. In each of the test formulations, probucol was dissolved in a peanut oil or a medium chain triglyceride, together with an ethanol cosolvent. These studies demonstrate that the vegetable oil-based formulations of the present invention exhibit better absorption characteristics than Lorelco® and the formulations prepared by Palin et al.

The following oil solutions of probucol were prepared on a weight percentage basis:

Formulation A: 10% probucol, 5% ethanol, 85% medium chain triglyceride (Captex 355, Karlshamns USA Inc. Columbus, Ohio).

Formulation B: 10% probucol, 5% ethanol, 85% peanut oil.

Formulation C: 10% probucol, 5% ethanol, 10% lecithin, 75% peanut oil.

The ethanol was added as a cosolvent to prevent precipitation of probucol from the peanut oil in formulations B & C. Probucol is, however, sufficiently soluble in medium chain triglycerides that ethanol was not required to prevent precipitation in formulation A. Ethanol was added to formulation A simply to ensure that, aside from the vegetable oil solvent, an essentially consistent composition was provided for comparison of the formulations.

In addition to the above formulations, a solid probucol control was used in the testing. The control was prepared by grinding Lorelco® tablets (from Marion Merrell Dow containing 64% w/w probucol) and forming a suspension in water at a concentration of about 100 mg per ml.

The above probucol formulations (three oil-based solutions and the control) were administered to adult Sprague-Dawley rats by gavage. In each case, probucol was administered in single doses to eight rats (4 male, 4 female) at the level of 100 mg/kg (100 milligrams of probucol per kilogram of animal body weight). The concentration of probucol in blood was monitored in each rat from plasma samples collected by retro-orbital sinus puncture. Measurements were taken prior to treatment and again at 1, 3, 6, 12, 18, 24 and 48 hours after treatment. The actual probucol concentration in plasma was determined by analytical high pressure liquid chromatography (HPLC) using a modification of the procedure described in Satonin & Coutant (D. K. Satonin and J. E. Coutant, *Comparison of gas chromatography and high performance liquid chromatography for the analysis of probucol in plasma*. Journal of Chromatography, 380, 401–406 (1986)). The detection limit of this technique was about 0.15 µg/ml. Any probucol concentration measurements below detectability were therefore assigned a value of 0.15 µg/ml for purposes of plotting.

Figure 2:
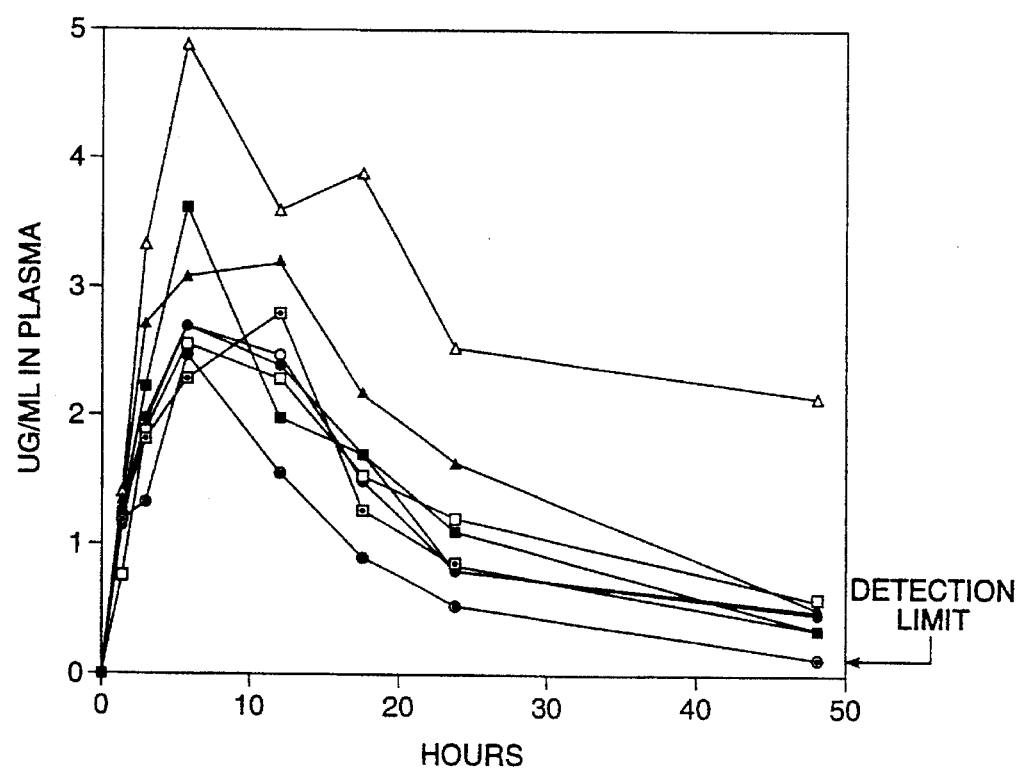
FIGS. 2 and 3 are graphs of probucol concentration in plasma versus time for an oil formulation (10% probucol in 85% peanut oil)
Figure 3:
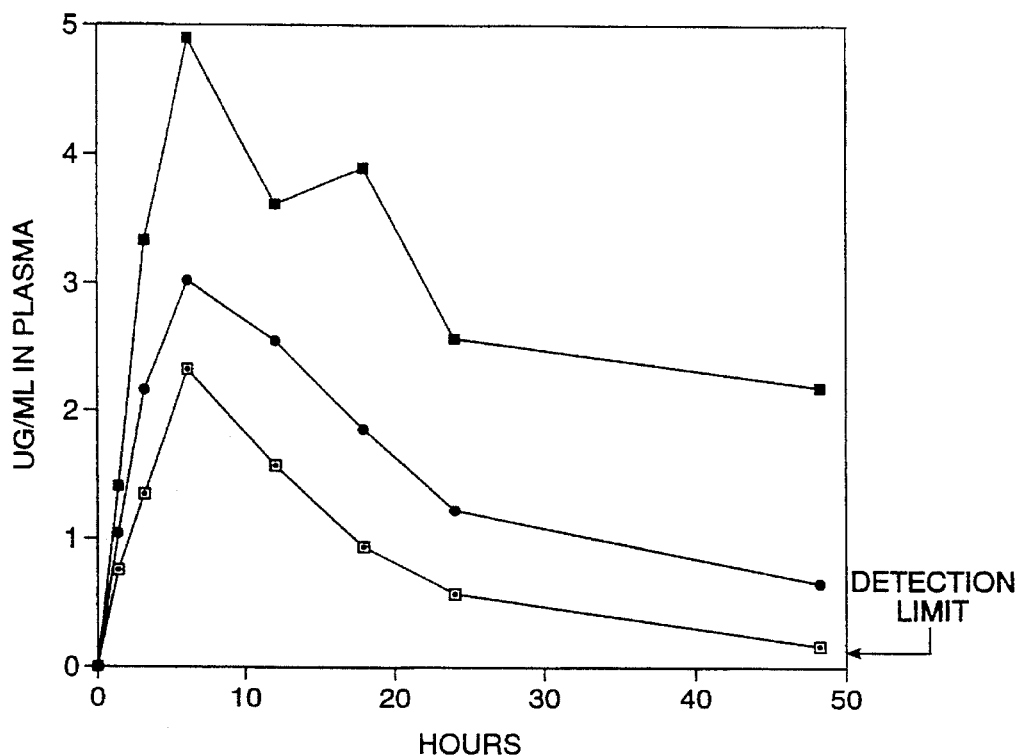
Figure 4:
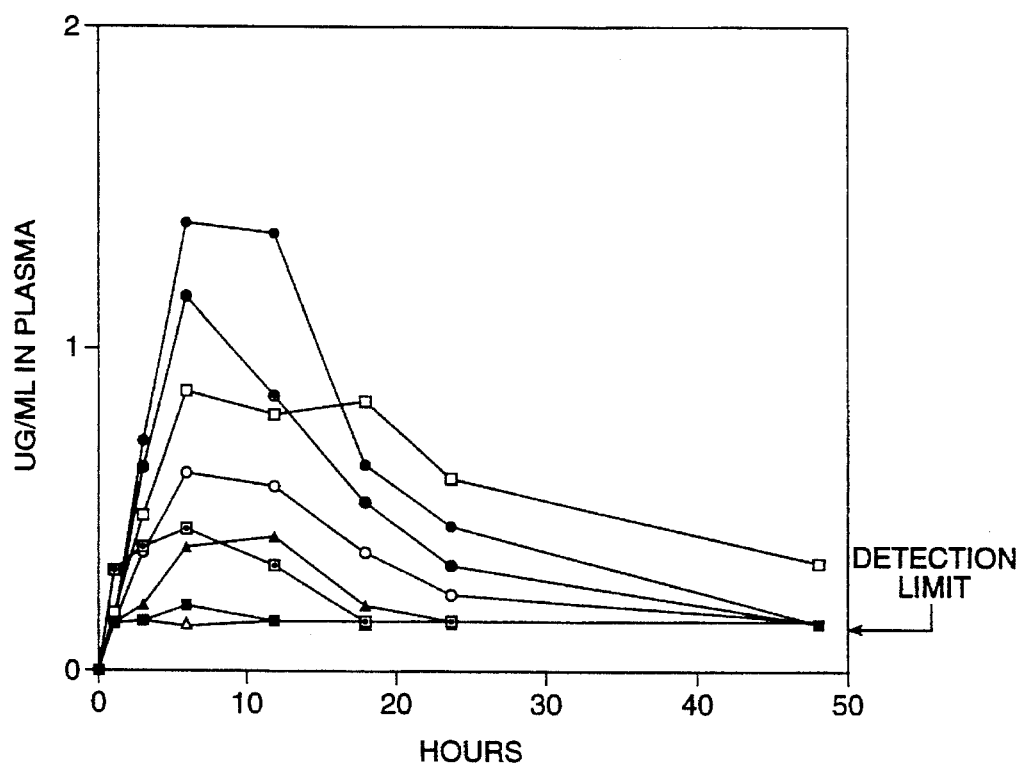
FIGS. 4 and 5 are graphs of plasma absorption versus time for probucol administered as Lorelco® at the dosage used with oil-based formulations 1–3.
Figure 5:
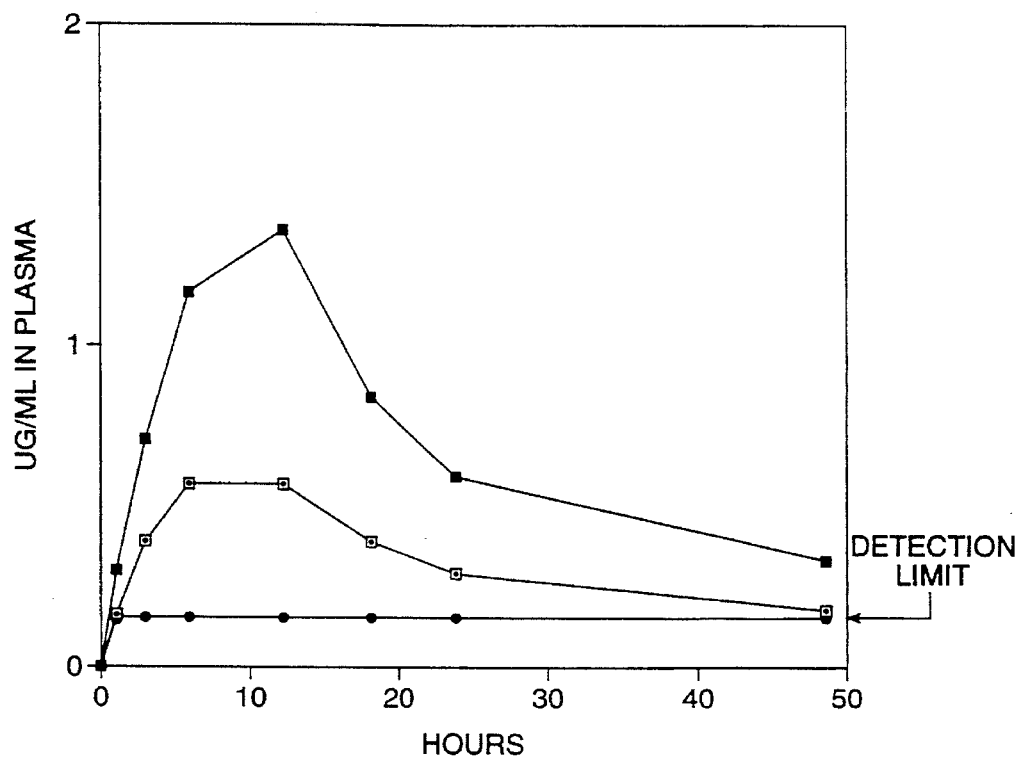

Plots showing the probucol concentration versus time for oil-based formulation B are presented in FIGS. 2 and 3. Corresponding plots for Lorelco® are presented in FIGS. 4 and 5. The first set of plots (FIGS. 2 and 4) display the serum probucol concentration versus time for each rat tested. The second set of plots (FIGS. 3 and 5), on the other hand, display the high, mean and low serum probucol concentrations among the eight rats at each time point. As can be seen from the mean (averaged) curves, the probucol in formulation B (FIG. 3) reaches a higher plasma concentration faster than the probucol in Lorelco® (FIG. 5). Formulations A and C behaved similarly.

Numerical results obtained from the mean (averaged) absorption curve for each probucol formulation are presented in Table 2.

TABLE 2

|  | Formulation | | | |
| --- | --- | --- | --- | --- |
|  | Lorelco | A | B | C |
| time to peak level of drug in serum | 10 hrs | 6 hrs | 6 hrs | 6 hrs |
| peak level (mean) of drug (µg/ml) | 0.6 hrs | 2.8 | 3.0 | 2.8 |
| variations from mean at peak: | | | | |
| high | +116% | +48% | +63% | +39% |
| low | +75% | +52% | −23% | −30% |
| area under curve (AUC), 0–48 hr. µg · hr · ml$^{-1}$ | 17 | 60 | 74 | 62 |

These results show that all three oil-based formulations exhibit significantly better levels of absorption, rates of absorption, and uniformity of absorption than the solid formulation. For all oil-based solutions tested, peak concentrations of probucol in blood were 4–5 times higher than those of Lorelco®. Likewise, the oil-based formulations gave a cumulative absorption (AUC) that was about 4 times higher the Lorelco® formulation. In addition, probucol in the oil-based formulations reached peak blood concentrations about 40% faster than probucol in Lorelco®. Finally, the oil-based formulations gave a more uniform absorption than Lorelco®.

The present study also shows that peanut oil and medium chain triglyceride perform similarly, and that their performance in the formulations of this invention is substantially better the performance of the solutions reported by Palin et al. The formulations of this invention reached peak concentrations of 2.8 to 3.0 µg/ml in six hours, whereas the Palin et al. solutions reached peak concentrations of only 1.73 µg/ml (0.54 µg/ml for the medium chain triglyceride solution) in five to seven hours.

The improvements observed with the oil-based formulations of this invention are important to the function of probucol. Faster absorption means that the therapeutic benefits to the patient will be manifested more quickly. Higher absorption levels mean that the administered probucol will be utilized more efficiently. Finally, greater uniformity of absorption from individual to individual means that the physiological effects of the dose are more predictable and the drug is rendered safer.

EXAMPLE II

Figure 6:
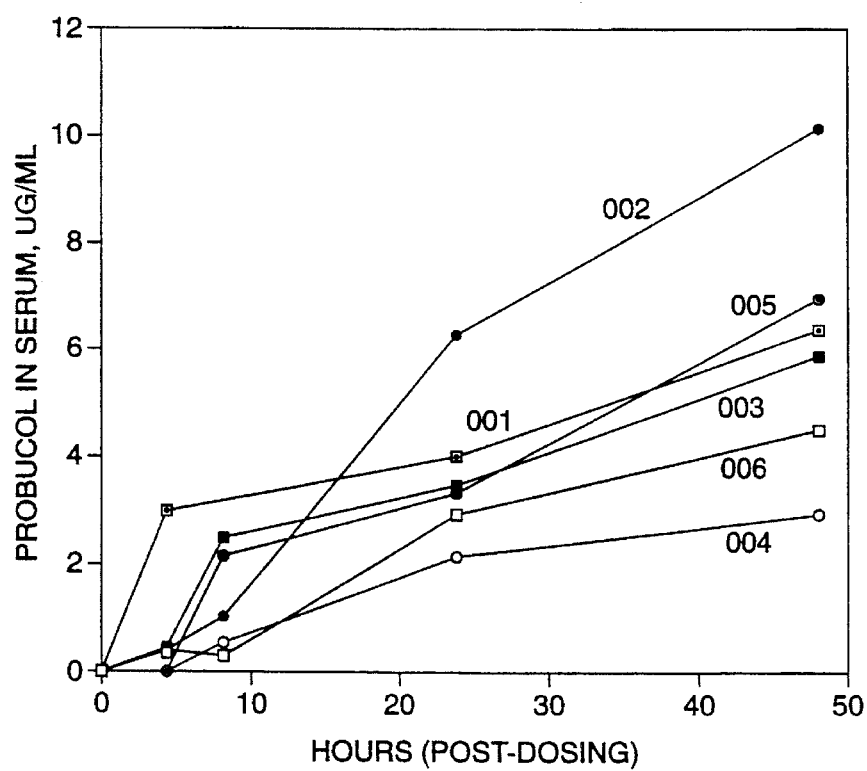
FIG. 6 is a graph of the average level of serum probucol versus time for the six patients administered an oil formulation of probucol.
Figure 7:
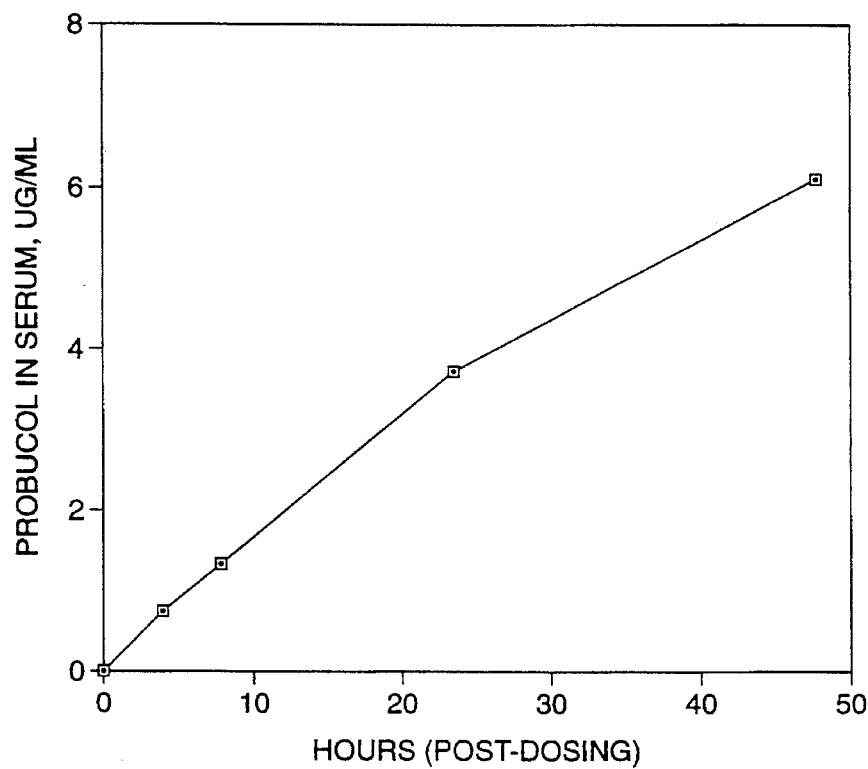
FIG. 7 is a graph of the average serum probucol concentration for the group of patients discussed in connection with FIG. 6.

Six HIV-infected patients were administered daily oral doses of 10% probucol in medium chain triglyceride. A first oral dose of 0.10 grams probucol in solution was given to each patient. Subsequently, the solution was administered in total daily dosages of 0.20 grams probucol. Following the first oral dosage of 0.10 grams probucol, blood samples were taken at four, eight, twenty-four, and forty-eight hours. The average level of serum probucol for the six patients versus time for each patient is presented in the graph of FIG. 6. The average serum concentration for the group of patients is presented in FIG. 7.

Other investigators have measured serum probucol concentration after a solid, tablet form of the drug was administered to human volunteers. See, J. F. Heeg and H. Tachizawa, *Plasma Levels of Probucol in Man After Single and Repeated Oral Dosages*, La Nouvelle Presse Medicale, 9:2990 (1990) (discussed above and referred to hereafter as "Heeg and Tachizawa"). A plot comparing the serum probucol levels from the probucol solution of this invention with those of Heeg and Tachizawa's probucol tablet ("Lorelco") is presented in FIG. 8.

Figure 8:
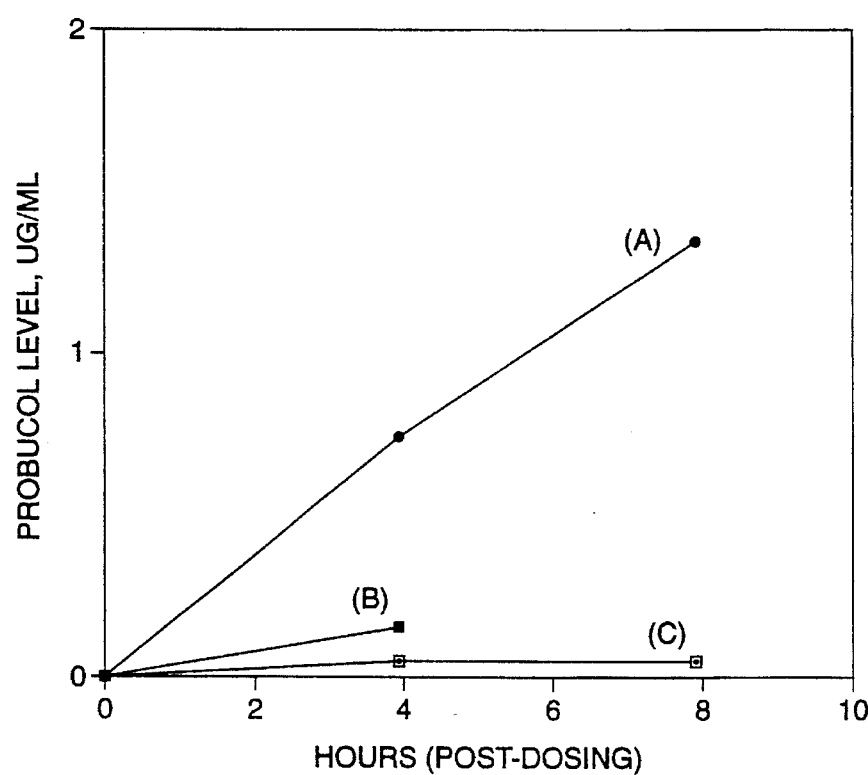
FIG. 8 is a plot comparing the serum probucol levels from the probucol solution of this invention with those of a probucol tablet.

Curve A in FIG. 8 represents averaged data for the six patients in the study. Each patient took an oral dose of 1.0 ml "PANAVIR" (100 mg probucol in medium chain triglyceride). Serum samples were analyzed by high pressure chromatography, (HPLC). At four and eight hours after administration of the single oral dose, the average serum Probucol concentrations were 0.73 µg/ml and 1.34 µg/ml respectively. The data for curve B was reported in Heeg and Tachizawa, in which six male volunteers each took a single 250 mg tablet. Blood samples were collected after four hours, at which time the average drug level was found to be 0.16 µg/ml. The data presented in curve C was also reported in Heeg and Tachizawa. This time a single 250 mg uncoated tablet was given to six male volunteers one-half hour before breakfast. The Probucol concentrations for this study were presented in a semilogarithmic plot. Probucol concentrations were estimated from the chart and then averaged to provide the data points in curve C. The average probucol concentration at four hours and at eight hours was estimated to be 0.045 µg/ml and 0.051 µg/ml respectively.

Thus, four hours after administration, the blood concentration of probucol in patients given 0.10 grams of probucol in the liquid formulation was between 4.6 and 16.2 times higher than the blood concentration of probucol in patients given 0.25 grams of Lorelco. In view of the results reported by Heeg and Tachizawa, It appears that the high serum-probucol concentrations resulting from the relatively low doses of the liquid probucol formulation were quite unexpected.

Figure 9:
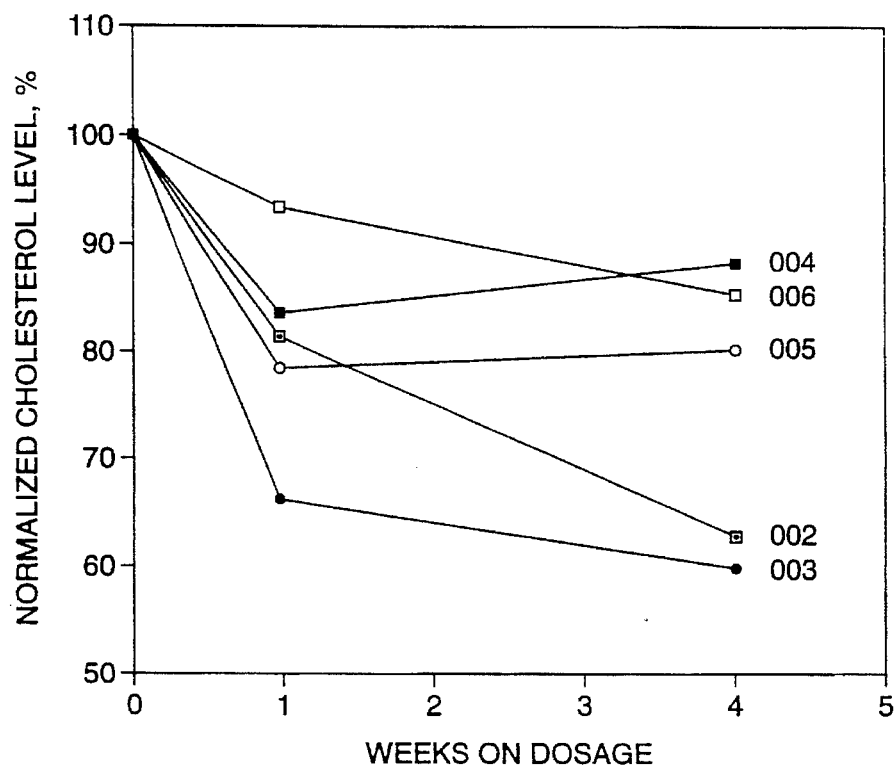
FIG. 9 is a graph of the cholesterol levels for five of the six patients discussed in connection with FIG. 6.
Figure 10:
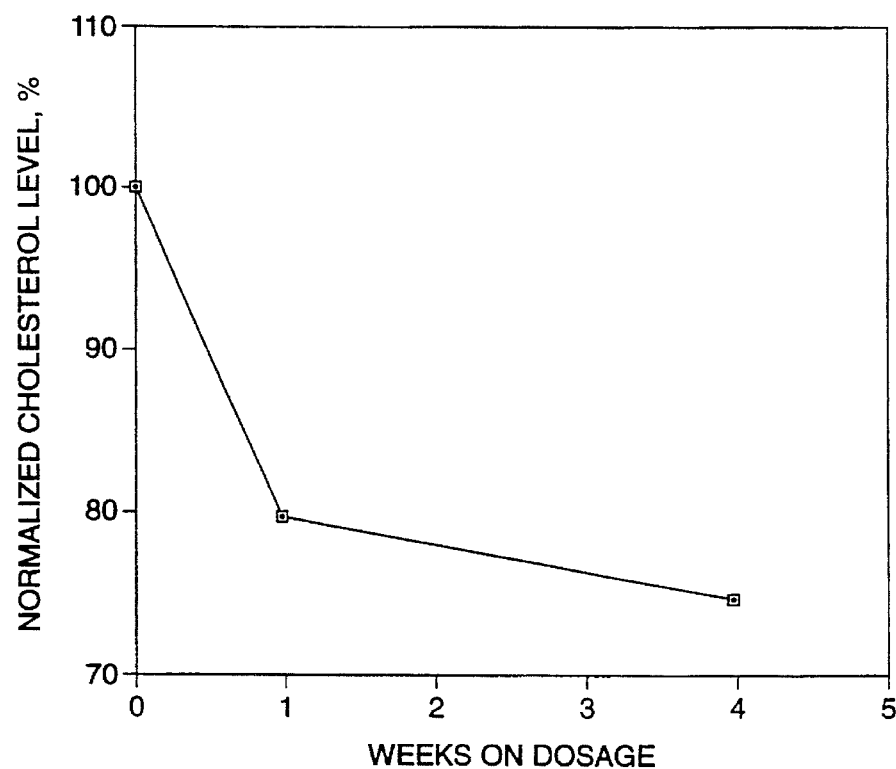
FIG. 10 is a graph of the average normalized cholesterol level of the data in FIG. 9.

Cholesterol levels of the six patient's in this study were also measured at one and four weeks. The patient's were given 0.20 grams of probucol solution daily, as described above. The graph presented in FIG. 9 summarizes the current laboratory information from five of the six HIV-infected patients in the study. Data on the sixth patient was incomplete and unverified, and therefore is not included here. The graph presented in FIG. 10 shows the average normalized cholesterol level for the five patients.

The data from the five patients shows an average 20% reduction of total cholesterol after one week and a 25% reduction after four weeks. This suggests that most of the drug effect is achieved over the first week after dosing begins, and that a plateau is approached after about four weeks.

EXAMPLE III

An FDA-sanctioned phase I clinical study of the antiviral effects of probucol/medium chain triglyceride solution in HIV infected patients was conducted for nine months. This was an open-label study, without the use of placebo, and with historical controls for comparison. In the study, a 10% solution of probucol in medium chain triglyceride (Captex ®355 from Karlshamns Lipid Specialties, Columbus, Ohio, USA) was administered orally to 19 patients having advanced HIV disease. On entry, the CD4+ cell counts ranged from >10 to 522. The average value was 170 and the median value was 77. Many of the patients had failed prior therapy with AZT, ddI or ddC, the only currently approved antiretroviral agents, and all were ineligible for therapy with these drugs. Therapeutic failures while on these drugs are typically due to the onset of toxic side effects or to the emergence of viral resistance to the drug.

The patients were mostly males ranging in age from 30 to 55 years, and were accrued as three sequential groups who were started on daily dosages of 200–210 mg/day, 400–420 mg/day, and 800 mg/day, respectively. Each patient was examined regularly, and the results of frequent clinical examinations and laboratory tests were recorded.

On the average, blood probucol levels in these patients were higher and were achieved more quickly than in patients in other studies who were given solid forms of the drug. For example, the patients given 400–420 mg/day reached an apparent blood plateau level of 19–20 ug/ml after two weeks. To reach the same plateau level with solid probucol requires a dosage of 1000 mg/day (the dose recommended for hypercholesterolemic patients) over a period of eight to twelve weeks.

At doses of 200–800 mg/day, no significant toxicities were encountered that were attributable to probucol. Some mild toxicities—principally diarrhea and flatulence—were encountered, but these are generally expected of probucol.

The effect that the probucol liquid formulation had on the progression of the disease was followed by tabulating several parameters, the most important of which were survival rate, CD4+ cells counts, p24 levels, and Quality of Life assessments. The first three of these parameters are summarized in the following table for the six patients who received 200–210 mg/day and who were on study for the longest period of time. Data for the studies at higher doses (400–420 mg/day and 800 mg/day) was available only for shorter periods of time.

|  | ENTRY | Dosage 200–210 mg/day | | | | | |
|---|---|---|---|---|---|---|---|
|  |  | MONTH 1 | MONTH 2 | MONTH 3 | MONTH 4 | MONTH 5 | MONTH 6 |
| Patient ID No. 1 |  |  |  |  |  |  |  |
| CD4 | <10 | <10 | <10 | <10 | <10 | <10 | <10 |
| P24 ANTIGEN | <10 | <10 | <10 | <10 | <10 | <10 | <10 |
| AVERAGE SCORE | 91.14 | 88.86 | 86.57 | 86.57 | 87.71 | 87.14 | 87.14 |
| Patient ID No. 2 |  |  |  |  |  |  |  |
| CD4 | 283 | 339 | 349 | 284 | 289 | 246 | 321 |

-continued

| | ENTRY | MONTH 1 | MONTH 2 | MONTH 3 | MONTH 4 | MONTH 5 | MONTH 6 |
|---|---|---|---|---|---|---|---|
| | | | | Dosage 200–210 mg/day | | | |
| P24 ANTIGEN | <10 | <10 | <10 | <10 | <10 | <10 | <10 |
| AVERAGE SCORE | 83.10 | 60.71 | 51.43 | 85.00 | 68.29 | 69.24 | 91.86 |
| Patient ID No. 3 | | | | | | | |
| CD4 | <10 | <10 | 22 | 10 | <10 | NOT DONE | DROPPED OUT OF STUDY |
| P24 ANTIGEN | 28.8 | 35.9 | 25 | 68 | 59 | NOT DONE | |
| AVERAGE SCORE | 48.10 | 46.67 | 41.52 | 50.19 | 37.81 | 28.90 | |
| Patient ID No. 4 | | | | | | | |
| CD4 | 99 | 55 | 59 | 48 | 42 | 44 | 48 |
| P24 ANTIGEN | 161 | 250 | 621 | 579 | 591 | 332 | 157 |
| AVERAGE SCORE | 33.76 | 60.48 | 66.53 | 60.19 | 48.19 | 54.26 | 15.71 |
| Patient ID No. 5 | | | | | | | |
| CD4 | 522 | 491 | 406 | 361 | 465 | 462 | 388 |
| P24 ANTIGEN | <10 | <10 | <10 | <10 | <10 | <10 | <10 |
| AVERAGE SCORE | 88.86 | 88.86 | 93.57 | 90.71 | 90.29 | 89.57 | 89.57 |
| Patient ID No. 6 | | | | | | | |
| CD4 | 77 | 92 | 72 | 59 | 48 | 40 | 38 |
| P24 ANTIGEN | <10 | <10 | <10 | <10 | <10 | <10 | <10 |
| AVERAGE SCORE | 34.10 | 37.24 | 67.76 | 30.33 | 22.00 | 24.10 | 33.95 |

No deaths occurred in this group. Some deaths did occur in the groups given higher doses, but for the most part these were not attributable to HIV progression. With an average CD4+ count of 167, and one-third of the 200–210 mg/day group with CD4+ counts below 10, this group of patients were advanced in the disease and were expected to have a high mortality rate. In comparison, a study with 20 patients on ddC therapy and an average CD4+ count on entry of 154 reported a death rate of 25% after 12 months (Yarchoan et al., Lancet:, Jan. 16, 1988, p.76). Another study with 159 patients on AZT therapy and an estimated average CD4+ count of 189 reported a death rate of 15% after one year. In the same study, 112 patients not receiving therapy and having an estimated average CD4+ count of 239 experienced a death rate: of 54% after one year (Vella et al., J.A.M.A. 267, (9), 1232(1992)). Consequently, the mortality rate in this study group appears to be significantly lower than in comparable historical controls.

CD4+ cell counts are subject to wide fluctuations, and the statistical significance of data from six patients during six months is weak. Nonetheless, it appears that three patients (1, 2, 3) held relatively steady in their CD4+ counts, and three patients (4, 5, 6) had slow decreases. It has been estimated from prior studies that HIV infection typically results in a decline in CD4+ cells at an overall rate of about 5–8 per month (Moss, Br. Med. J., 29, 1067 (1988)) although the rate varies between patients, and typically occurs at an accelerated rate in later stages of the disease as CD4+ counts fall below about 400 (Miedema et al., HIV and the Immune System, R. B. Gallagher, Ed., Elsevier Trends Journals, 1991, p.89; Fauci et al., Annals of Internal Medicine, 114(8), 678 (1991)). The net rate of CD4+ cell decline in this study group appears to be lower than in historical comparisons.

Increases in p24 antigen are usually associated with increases in viral load and viral replication in HIV infected patients. Such increases are most likely to occur in patients whose CD4+ counts fall below about 200–300, and they generally indicate an increased probability of opportunistic infection and death (Fauci et al., Annals of Internal Medicine, 114(8), 678 (1991); MacDonell et al., Am. J. Med., 89 (6), 706 (1990)). p24 antigen levels are also subject to wide fluctuations, and have weak statistical significance in small patient groups. In this study group, however, four of the six patients did not show any transient or net increase in p24. Two patients (3, 4) showed transient increases, and only one of the patients (3) appeared to show a net increase. Viral replication therefore does not appear to have accelerated substantially in any of these patients.

A Quality of Life questionnaire, previously validated for use in HIV studies (Wachtel et al., Annals of Internal Medicine, 116, 129 (1992)) was periodically given to the patients in order to assess various aspects of their functional capacity and well-being. The overall (average) scores over the duration of the study were substantially constant for most of the patients (1, 2, 5, 6) and may have decreased for two of the patients (3, 4).

The above data shows that patients receiving the probucol formulation of this invention—particularly in doses of 200–210 mg/day—remain relatively stable, even though they were quite advanced in their HIV disease at entry and would have been expected to deteriorate substantially during the six month study period discussed.

CONCLUSION

Although the above discussion has focused on certain preferred embodiments of the present invention, some variations of the formulation and method will be apparent to those skilled in the art. For example, the probucol formulations of the present invention could be employed to treat viral infections or high cholesterol levels in a variety of mammals other than humans and rats. In addition, the formulations of this invention may, in some instances, be used to administer phenolic anitoxidants other than probucol. These and other modifications are intended to be included within the scope of the claims appended hereto.

What is claimed is:

1. A lipophilic pharmaceutical formulation for oral administration consisting essentially of a digestible medium chain triglyceride and probucol, said probucol having a concentration greater than about 5% by weight, and said probucol being completely dissolved in said digestible medium chain triglyceride.

2. The lipophilic pharmaceutical formulation recited in claim 1 wherein said formulation includes ethanol.

3. The lipophilic pharmaceutical formulation recited in claim 2 wherein said ethanol is present in a concentration of less than about 10% by weight.

4. The lipophilic pharmaceutical formulation recited in claim 3 wherein said probucol is present in an amount of between about 5 and 15% by weight and said medium chain triglyceride is present in an amount of greater than about 80% by weight of said solution.

5. The lipophilic pharmaceutical formulation recited in claim 3 wherein said ethanol is present in a concentration of about 5% by weight.

6. The lipophilic pharmaceutical formulation recited in claim 1 wherein said probucol is present in an amount of between about 5 and 15% by weight and said medium chain triglyceride is present in an amount of greater than about 80% by weight of said solution.

7. The lipophilic pharmaceutical formulation recited in claim 1 wherein said medium chain triglyceride has fatty acid chains each with 6 to 12 carbon atoms.

8. The lipophilic pharmaceutical formulation recited in claim 1 wherein said probucol is present in an amount of between about 8% and 13% by weight.

9. A method for increasing probucol absorption by an organism, said method comprising orally administering to the organism a solution consisting essentially of greater than about 5% by weight probucol dissolved in a digestible medium chain triglyceride.

10. The method recited in claim 9 wherein said solution includes ethanol.

11. The method recited in claim 10 wherein said ethanol is present in a concentration of less than about 10% by weight.

12. The method recited in claim 11 wherein said probucol is present in an amount of between about 5 and 15% by weight and said medium chain triglyceride is present in an amount of greater than about 80% by weight of said solution.

13. The method recited in claim 11 wherein said ethanol is present in a concentration of about 5% by weight.

14. The method recited in claim 9 wherein said probucol is present in an amount of between about 5 and 15% by weight and said medium chain triglyceride is present in an amount of greater than about 80% by weight of said solution.

15. The method recited in claim 9 wherein said medium chain triglyceride has side chains with 6 to 12 carbon atoms.

16. The method recited in claim 9 wherein said organism is a human.

17. The method recited in claim 16 wherein probucol is administered in single doses of between about 5 and about 40 mg probucol/kg body weight.

18. The method recited in claim 16 wherein probucol is administered in a dose of between about 100 and 1000 mg/day.

* * * * *